US012779242B2

(12) United States Patent
Song et al.

(10) Patent No.: US 12,779,242 B2
(45) Date of Patent: Nov. 3, 2026

(54) METHOD AND DEVICE FOR GENERATING ANTICANCER MATERIAL IN LIVING BODY

(71) Applicant: RESEARCH & BUSINESS DEVELOPMENT FOUNDATION, SOOKMYUNG WOMEN'S UNIVERSITY, Seoul (KR)

(72) Inventors: Seung Hyun Song, Seoul (KR); Albert Kim, Philadelphia, PA (US)

(73) Assignee: Research & Business Development Foundation, Sookmyung Women's University, Seoul (KR)

(*) Notice: Subject to any disclaimer, the term of this patent is extended or adjusted under 35 U.S.C. 154(b) by 814 days.

(21) Appl. No.: 18/070,465

(22) Filed: Nov. 28, 2022

(65) Prior Publication Data

US 2023/0087484 A1 Mar. 23, 2023

Related U.S. Application Data

(63) Continuation of application No. PCT/KR2021/006720, filed on May 31, 2021.

(30) Foreign Application Priority Data

Jun. 1, 2020 (KR) ........................ 10-2020-0065967

(51) Int. Cl.
*A61N 5/06* (2006.01)

(52) U.S. Cl.
CPC ......... *A61N 5/0613* (2013.01); *A61N 5/0601* (2013.01); *A61N 2005/0661* (2013.01)

(58) Field of Classification Search
CPC ................ A61N 5/0613; A61N 5/0601; A61N 2005/0661
See application file for complete search history.

(56) References Cited

U.S. PATENT DOCUMENTS

2004/0059388 A1* 3/2004 Herbst ..................... A61N 1/32 607/2

FOREIGN PATENT DOCUMENTS

WO WO-2010091074 A2 * 8/2010 ............... A61N 1/32
WO WO-2015006309 A1 * 1/2015 ............. A61B 18/24
WO WO-2015073885 A1 * 5/2015 ............. A61B 18/02

OTHER PUBLICATIONS

Rosenberg et al. Inihibition of Cell Division in *Escherichia coli* by Electrolysis Products from a Platinum Electrode, Nature, Biophysics, vol. 205, pp. 698-699 Feb. 13, 1965. (Year: 1965).*
R. J. Browning, P. J. T. Reardon, M. Parhizkar, R. B. Pedley, M. Edirisinghe, J. C. Knowles, E. Stride, ACS Nano 2017, 11, 8560.

(Continued)

*Primary Examiner* — Erica S Lee
(74) *Attorney, Agent, or Firm* — Nicholas Park

(57) ABSTRACT

A device inserted into a living body to generate an anticancer material is disclosed. The disclosed device comprises: an electric energy converter which receives an external signal to convert the external signal into electric energy; at least one electrode pair for causing electrolysis in a body fluid inside the living body by using the electric energy converted by the electric energy converter; and a light emitter for emitting light at a by-product produced by means of electrolysis by using the electric energy converted by the electric energy converter.

19 Claims, 16 Drawing Sheets

(56) References Cited

OTHER PUBLICATIONS

S. H. Song, A. Kim, B. Ziaie, IEEE Trans. Biomed. Eng. 2015, 62, 2717.

A. Kim, S. K. Lee, T. Parupudi, R. Rahimi, S. H. Song, M. C. Park, S. Islam, J. Zhou, A. K. Majumdar, J. S. Park, J. M. Yoo, B. Ziaie, Sci. Rep. 2020, 10, 1510.

* cited by examiner

METHOD AND DEVICE FOR GENERATING ANTICANCER MATERIAL IN LIVING BODY

CROSS-REFERENCE TO RELATED APPLICATION

This application is a US Bypass Continuation Application of International Application No. PCT/KR2021/006720, filed on May 31, 2021, and designating the United States, the International Application claiming a priority date of Jun. 1, 2020, based on prior Korean Application No. 10-2020-0065967, filed on Jun. 1, 2020, the disclosure of which is incorporated herein by reference in its entirety.

BACKGROUND

Technical Field

The following description relates to a method and device for generating an anticancer substance, and more particularly to technology for generating an anticancer substance by injecting a small device into a living body and by driving the small device using an ultrasonic signal generated outside to thereby cause an electrolysis reaction inside the living body.

Related Art

Cancer is a representative disease that has not yet been conquered. As a method of treating cancer, there is a method that uses an anticancer drug. However, most anticancer drugs have side effects not only on cancer cells but also on normal cells. Typical side effects include hair loss, nausea, vomiting, kidney dysfunction, tinnitus, and hearing loss.

To minimize side effects of an anticancer drug, studies have been conducted to locally administer the anticancer drug to an area in which cancer cells are present. One of such attempts is a method of inserting a pump and locally delivering the anticancer drug. However, since a size of the pump is large, this also causes great pain to a patient.

Also, although a small device is to be inserted, there are some limitations in reducing a size of a part, such as a battery required for the device. Also, due to an insufficient amount of anticancer drug synthesized by the device, performance of the anticancer drug is degraded.

SUMMARY

Technical Problem

According to at least one example embodiment, disclosed is a method and device for generating an anticancer substance by injecting a small device into a living body and by driving the small device using an ultrasonic signal generated outside to thereby cause an electrolysis reaction inside the living body.

Technical Solution

According to an aspect, disclosed is a device for inserting into a living body and generating an anticancer substance. The device includes an electric energy converter configured to receive an external signal and to convert the external signal to electric energy; at least one electrode pair configured to cause electrolysis in a body fluid inside the living body using the electric energy converted by the electric energy converter; and a light emitter configured to emit light to by-product by the electrolysis using the electric energy converted by the electric energy converter.

The electric energy converter may be configured to receive an ultrasonic signal generated outside the living body and to convert the ultrasonic signal to the electric energy.

The electric energy converter may include a piezoelectric element configured to receive the ultrasonic signal.

The electrode pair may contain platinum, at least a portion of the electrode pair may generate platinum cations in the electrolysis process, and the anticancer substance may be a platinum-based anticancer substance.

The device may further include a rectifying circuit configured to convert current generated by the electric energy converter to one-way current and to supply the same to the electrode pair.

The light emitter may be configured to emit ultraviolet light.

The light emitter may be configured to induce a chemical reaction between the by-product and ions contained in the body fluid of the living body by emitting the ultraviolet light to the by-product by the electrolysis.

The by-product by the electrolysis may contain platinum cations. The anticancer substance generated by a chemical reaction between the platinum cations and ions contained in the body fluid of the living body may contain cisplatin.

According to another aspect, disclosed is a device for generating an anticancer substance in a living body. The disclosed device includes a signal generator configured to generate an energy transfer signal outside the living body; and an anticancer substance generator configured to insert into the living body and to generate an anticancer substance using the energy transfer signal received from the signal generator.

The anticancer substance generator includes an electric energy converter configured to receive an external signal and to convert the external signal to electric energy; at least one electrode pair configured to cause electrolysis in a body fluid inside the living body using the electric energy converted by the electric energy converter; and a light emitter configured to emit light to by-product produced by the electrolysis using the electric energy converted by the electric energy converter.

The signal generator may be configured to generate an ultrasonic signal, and the electric energy converter may be configured to receive the ultrasonic signal generated outside the living body and to convert the ultrasonic signal to the electric energy.

The electric energy converter may include a piezoelectric element configured to receive the ultrasonic signal.

The electrode pair may contain platinum, at least a portion of the electrode pair may generate platinum cations in the electrolysis process, and the anticancer substance may be a platinum-based anticancer substance.

The anticancer substance generator may further include a rectifying circuit configured to convert current generated by the electric energy converter to one-way current and to supply the same to the electrode pair.

The light emitter may be configured to emit ultraviolet light.

The light emitter may be configured to induce a chemical reaction between the by-product and ions contained in the body fluid of the living body by emitting the ultraviolet light to the by-product by the electrolysis.

The by-product by the electrolysis may contain platinum cations. The anticancer substance generated by a chemical reaction between the platinum cations and ions contained in the body fluid of the living body may contain cisplatin.

DETAILED DESCRIPTION

Figure 1:
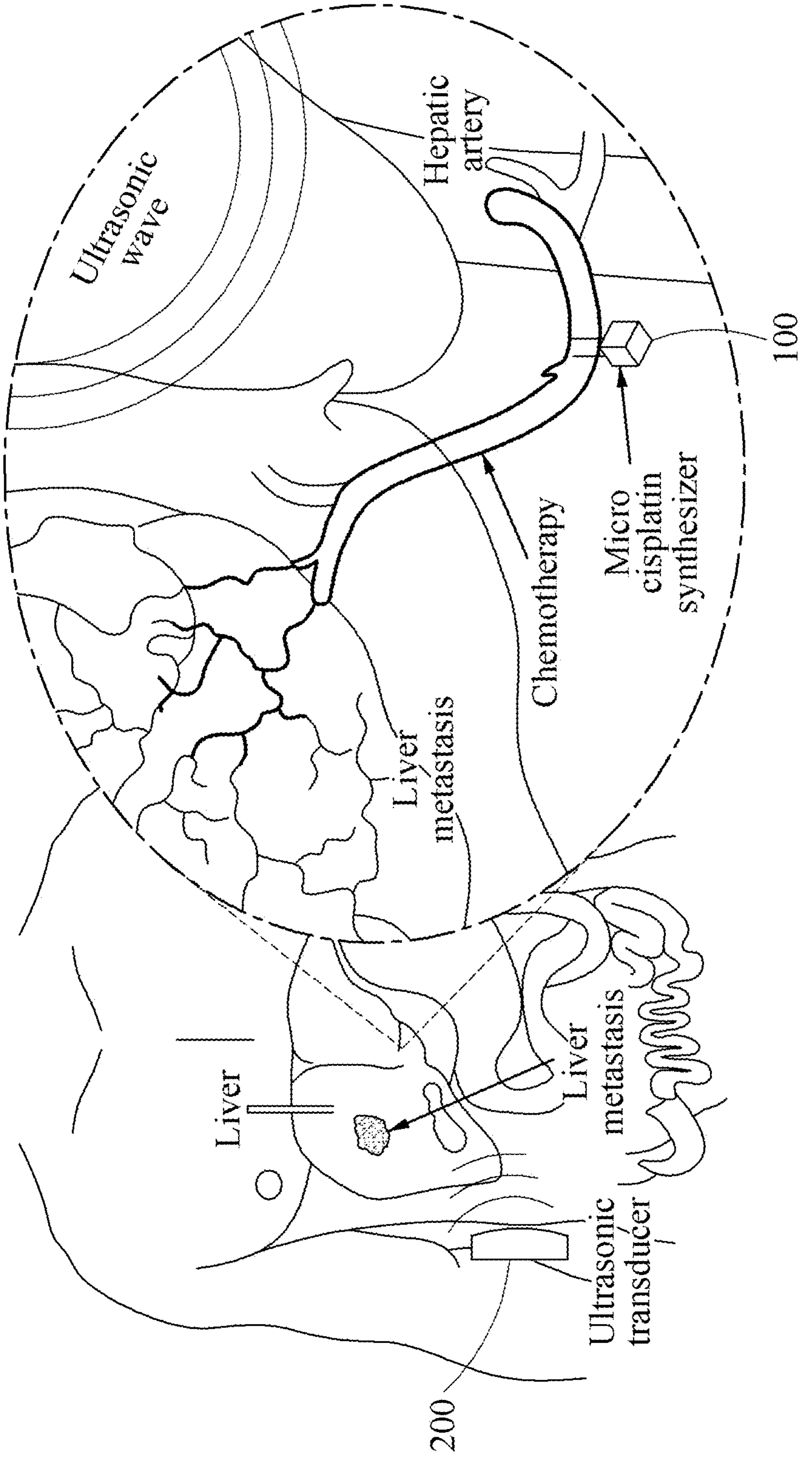
FIG. 1 illustrates an example of locally generating an anticancer substance inside a living body using an anticancer substance generation device according to an example embodiment.

Specific structural or functional description related to example embodiments are provided for examples only and the example embodiments may be variously modified and implemented. Therefore, the example embodiments are not construed as limited to specific implementation and the scope of the present specification includes all changes, equivalents, and replacements within the idea and the technical spirit.

Although terms of "first," "second," and the like are used to explain various components, the components are not limited to such terms. These terms are used only to distinguish one component from another component. For example, a first component may be referred to as a second component, or similarly, the second component may be referred to as the first component.

When it is mentioned that one component is "connected" to another component, it may be understood that the one component is directly connected or accessed to another component or that still other component is present between the two components.

As used herein, the singular forms "a," "an," and "the" are intended to include the plural forms as well, unless the context clearly indicates otherwise. It will be further understood that the terms "comprises" or "comprising," when used in this specification, specify the presence of stated features, integers, steps, operations, elements, components or a combination thereof, but do not preclude the presence or addition of one or more other features, integers, steps, operations, elements, components, or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

Hereinafter, example embodiments will be described in detail with reference to the accompanying drawings. Describing with reference to the accompanying drawings, like reference numerals refer to like elements throughout and repeated description related thereto is omitted.

FIG. 1 illustrates an example of locally generating an anticancer substance inside a living body using an anticancer substance generation device according to an example embodiment.

Referring to FIG. 1, the anticancer substance generation device may include a signal generator 200 and an anticancer substance generator 100.

The signal generator 200 may generate a signal outside a living body. The signal generator 200 may generate a signal and may deliver energy to the anticancer substance generator 100 positioned inside the living body. For example, the signal generator 200 may generate a radio signal, such as an electromagnetic wave and an ultrasonic wave, and may deliver energy to the anticancer substance generator 100.

When the signal generator 200 generates an ultrasonic signal, the signal generator 200 may more effectively deliver the energy to the anticancer substance generator 100 inside the living body. The radio signal generated by the signal generator 200 may lose its strength while passing through the living tissue. However, when the signal generator 200 delivers the energy using the ultrasonic signal, the attenuation of the signal may decrease while the ultrasonic signal penetrates the living tissue. For example, when the signal generator 200 generates an optical signal or an electromagnetic signal, a penetration depth of the signal in the living tissue may be small and energy transfer efficiency may decrease accordingly. In contrast, when the signal generator 200 generates the ultrasonic signal, the penetration depth of the signal in the living tissue may be large and the energy transfer efficiency may increase accordingly.

For example, the signal generator 200 may make energy per unit area of a signal delivered to the surface of the living body be 750 $mW/cm^2$ or less. This is based on US FDA standards. However, the example embodiment is not limited thereto. In an extreme situation, the signal generator 200 may make energy per unit area of the signal delivered to the surface of the living body be 750 $mW/cm^2$ or more.

The signal generator 200 may generate the ultrasonic signal. A frequency of the ultrasonic signal may be around about 2.3 MHz. However, it is provided as an example only, the frequency of the ultrasonic signal may vary in the range of different numerical values. The signal generator 200 may include a module configured to generate a seed signal inside, an amplification module configured to amplify the seed signal, an impedance matching circuit, and a piezoelectric bulk ceramic. However, it is provided as an example only and the signal generator 200 may be changed with components that may be easily employed by one skilled in the art to generate the ultrasonic signal.

The anticancer substance generator 100 may be injected into the living body. The anticancer substance generator 100 may be injected through a biopsy needle. The anticancer substance generator 100 may have a size similar to a size of a grain of rice. Therefore, the anticancer substance generator 100 may have a size suitable for injection into the living body through the biopsy needle.

The anticancer substance generator 100 may be injected into the living body and may reach near cancer cells. As another example, the anticancer substance generator 100 may be injected into the blood vessel that supplies blood to the cancer cells. For example, referring to FIG. 1, the anticancer substance generator 100 may be injected into the hepatic artery. The anticancer substance generator 100 may locally generate an anticancer substance.

The anticancer substance generator 100 may receive the signal generated by the signal generator 200 outside the living body. For example, the anticancer substance generator 100 may receive the ultrasonic signal. The anticancer substance generator 100 may convert the received ultrasonic signal to electric energy. The anticancer substance generator 100 may cause a chemical reaction with electrolysis inside the living body using the electric energy.

Figure 2:
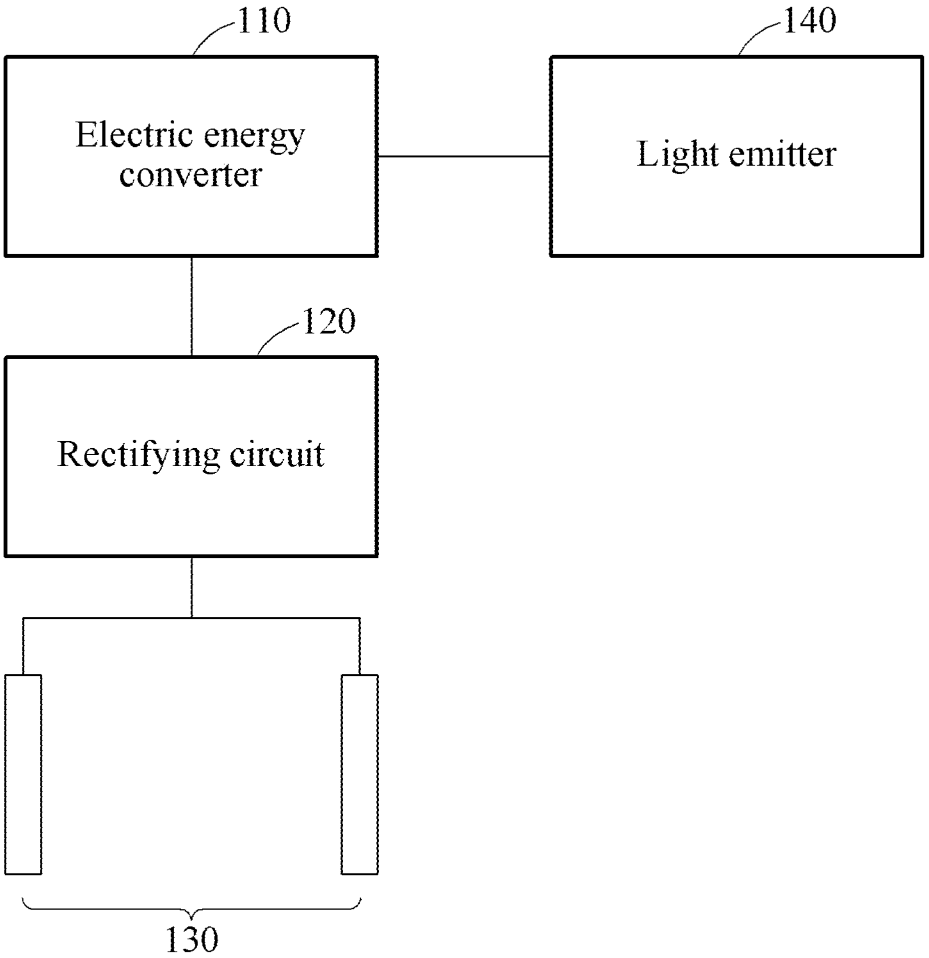
FIG. 2 is a diagram illustrating a configuration of an anticancer substance generator according to an example embodiment.

FIG. 2 is a diagram illustrating a configuration of the anticancer substance generator 100 according to an example embodiment.

Referring to FIG. 2, the anticancer substance generator 100 may include an electric energy converter 110, a light emitter 140 supplied with power from the electric energy converter 110 and configured to emit light, a rectifying circuit 120 supplied with power from the electric energy converter 110 and configured to provide one-way current, and an electrode pair 130 supplied with current from the rectifying circuit 120 and configured to perform electrolysis.

The electric energy converter 110 may receive a signal generated by the signal generator 200. The electric energy converter 110 may receive the signal of the signal generator 200 and may convert the signal to electric energy. The electric energy converter 110 may generate the current. The electric energy converter 110 may receive an ultrasonic wave and may convert the ultrasonic wave to the electric energy. To this end, the electric energy converter 110 may include a piezoelectric element.

The rectifying circuit 120 may receive the current from the electric energy converter 110 and may convert the current to the one-way current. Here, the one-way current may include direct current (DC) as current that flows in one direction. For example, the electric energy converter 110 may receive an ultrasonic wave and may generate alternating current (AC). The rectifying circuit 120 may receive the AC and may convert the AC to the DC. The DC output from the rectifying circuit 120 may be delivered to the electrode pair 130.

The electrode pair 130 may include an anode electrode and a cathode electrode. In the anode electrode, a metal may be oxidated. The electrode pair 130 may cause an electrolysis reaction in the body fluid of the living body. At least a portion of the electrode pair 130 may include platinum. Therefore, platinum cations may be delivered to the body fluid of the living body due to the oxidation reaction. In this case, the anticancer substance generator 100 may generate a platinum-based anticancer substance. However, the example embodiment is not limited thereto. At least a portion of the electrode pair 130 may include a different metal. In the electrolysis process, other metal cations may be delivered to the body fluid of the living body. An electrolysis by-product caused by the electrode pair 130 may be a precursor for synthesizing the anticancer substance.

The light emitter 140 may emit light to the electrolysis by-product using the electric energy acquired from the electric energy converter 110. The light emitter 140 may be directly connected to the electric energy converter 110, and may be connected to the electric energy converter 110 through the rectifying circuit 120. For example, the light emitter 140 may emit ultraviolet light. When the light emitter 140 emits light to the electrolysis by-product, a chemical reaction between the electrolysis by-product and an ionized material contained in the body fluid of the living body may be promoted. An anticancer drug may be synthesized through the chemical reaction.

FIGS. 3A to 3D illustrate a first example of a manufacturing process of the anticancer substance generator 100.

Figure 3A:
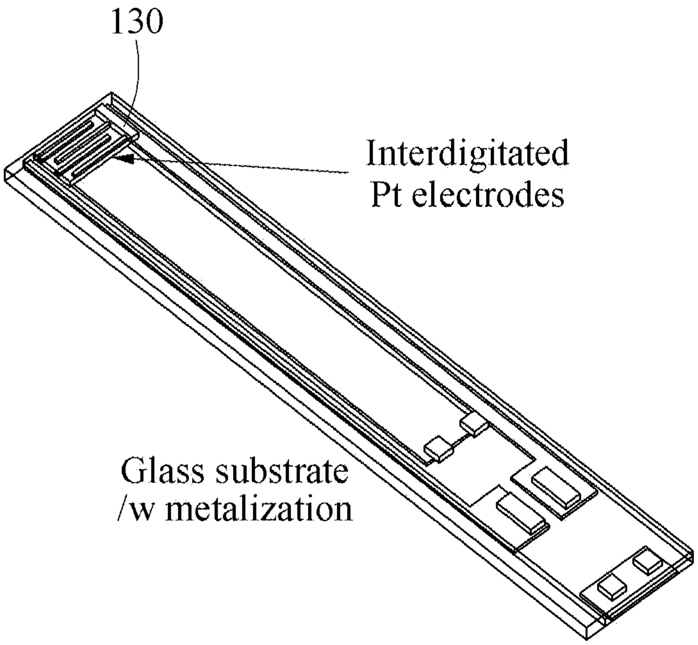
FIGS. 3A to 3D illustrate a first example of a manufacturing process of an anticancer substance generator.
Figure 3B:
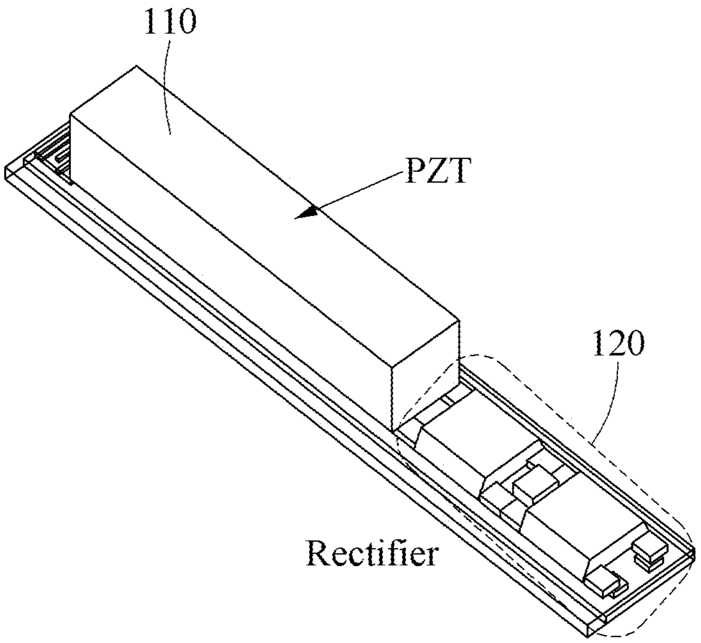
Figure 3C:
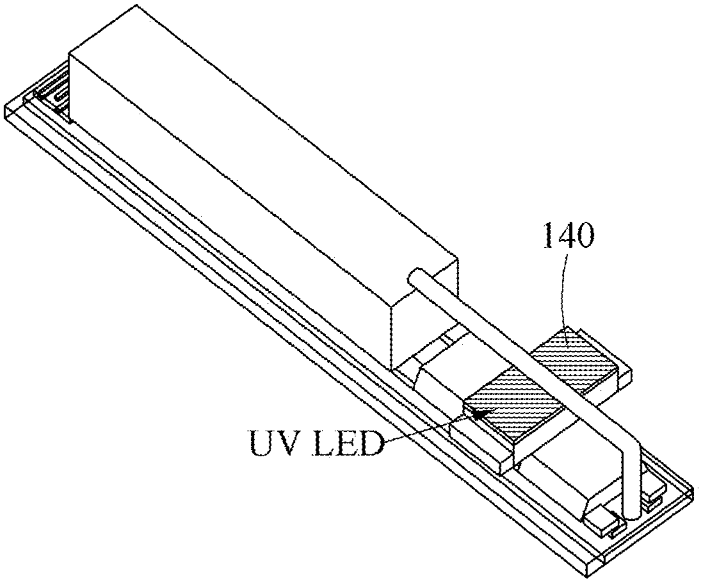
Figure 3D:
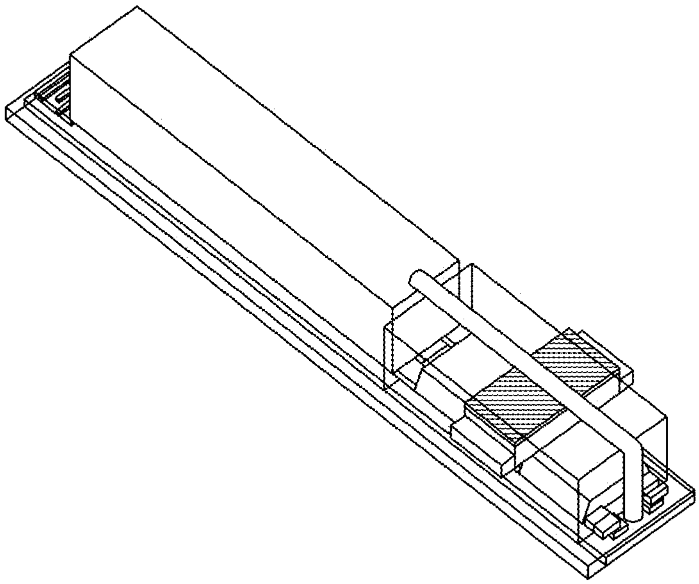

Referring to FIG. 3A, the electrode pair 130 may be installed on a substrate. The electrode pair 130 may include a platinum (Pt) material. Referring to FIG. 3B, the electric energy converter 110 and the rectifying circuit 120 may be installed on the substrate. The electric energy converter 110 may include a piezoelectric element (PZT). The electric energy converter 110 may receive an ultrasonic wave and may generate current. The rectifying circuit 120 may convert the current generated by the electric energy converter 110 to DC and may deliver the DC to the electrode pair 130. Referring to FIG. 3, the light emitter 140 may be installed. The light emitter 140 may include a light emitting diode (LED) configured to emit ultraviolet (UV) light. Referring to FIG. 3D, a cover may be installed to protect the light emitter 140 and the rectifying circuit 120.

FIGS. 4A to 4D illustrate a second example of a manufacturing process of the anticancer substance generator 100.

Figure 4A:
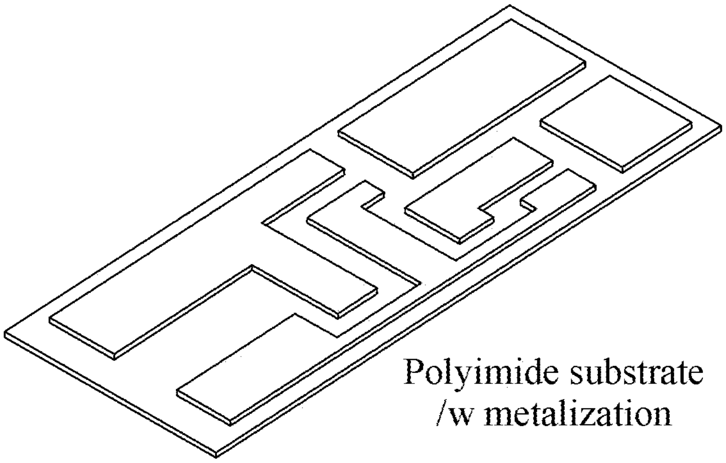
FIGS. 4A to 4D illustrate a second example of a manufacturing process of an anticancer substance generator.
Figure 4B:
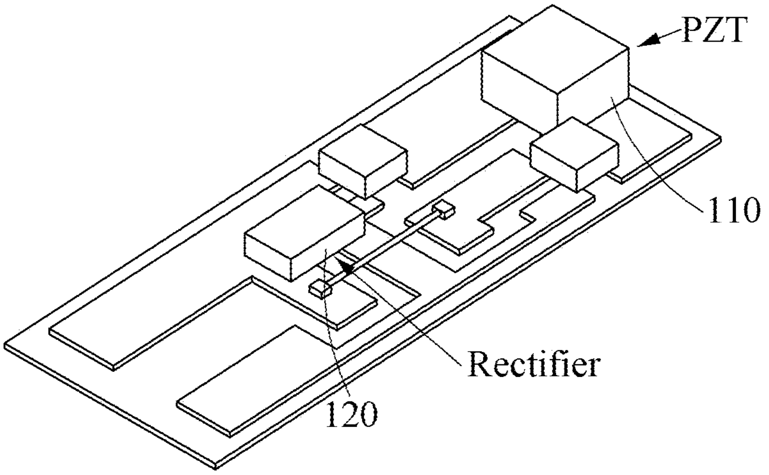
Figure 4C:
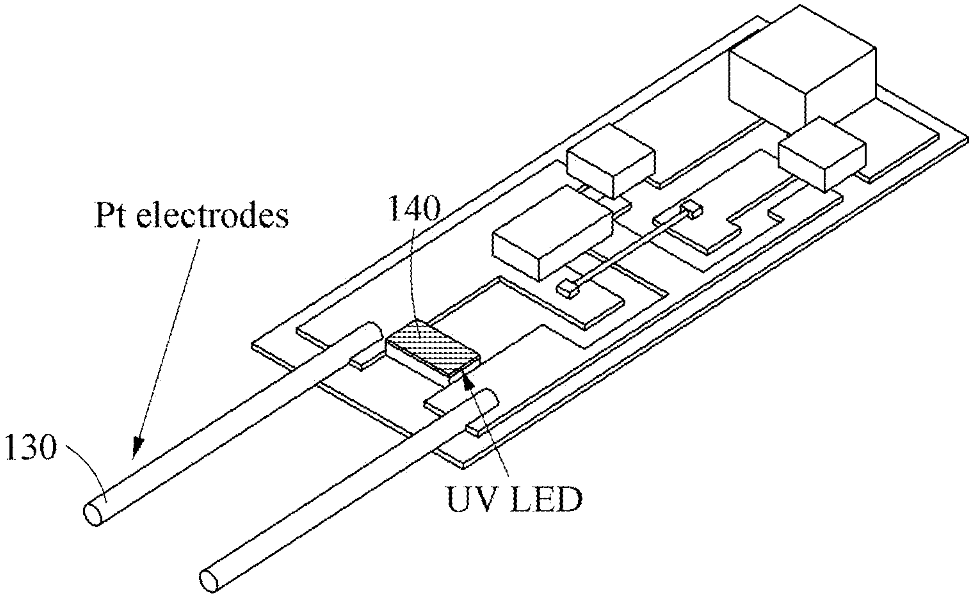
Figure 4D:
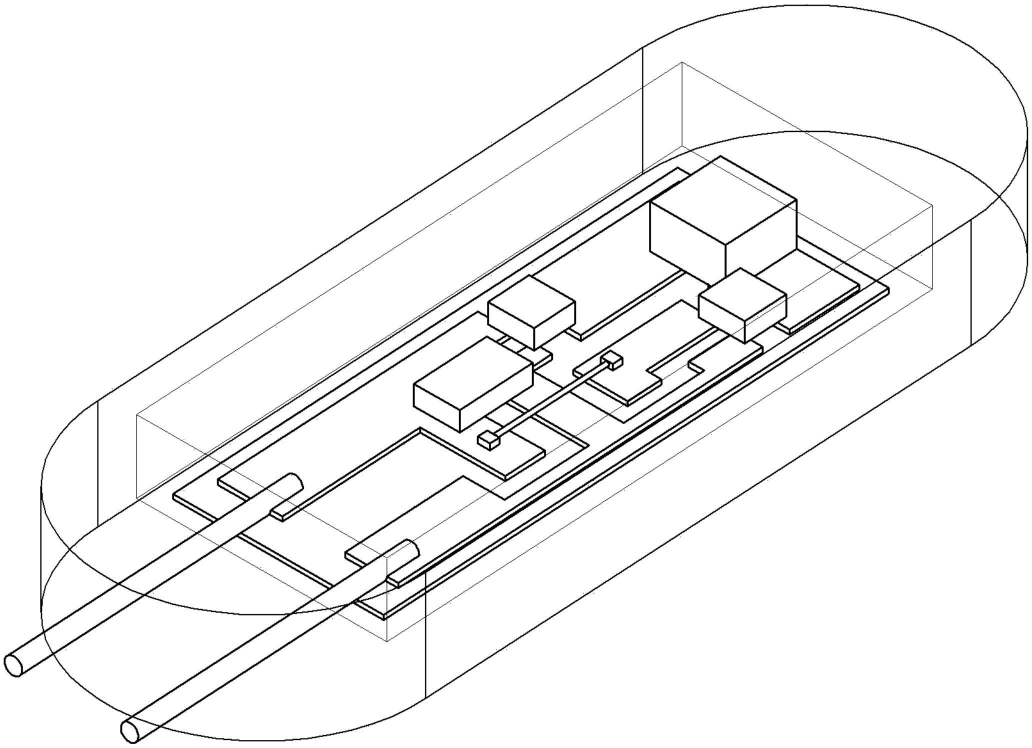

Referring to FIG. 4A, a polyimide substrate may be provided. Referring to FIG. 4B, the rectifying circuit 120 and the electric energy converter 110 may be installed on the substrate. Referring to FIG. 4C, the electrode pair 130 may be installed. The electrode pair 130 may be connected to the rectifying circuit 120 or the electric energy converter 110. Also, referring to FIG. 4D, the light emitter 140 may be installed. The light emitter 140 may be connected to the rectifying circuit 120 or the electric energy converter 110.

The aforementioned manufacturing process of the anticancer substance generator 100 and shape of the anticancer substance generator 100 are provided as an example only to describe the example embodiment and the scope of the present invention is not limited thereto. A detailed shape and manufacturing process of the anticancer substance generator 100 may be changed within the range easily modifiable by one of ordinary skill in the art.

Figure 5A:
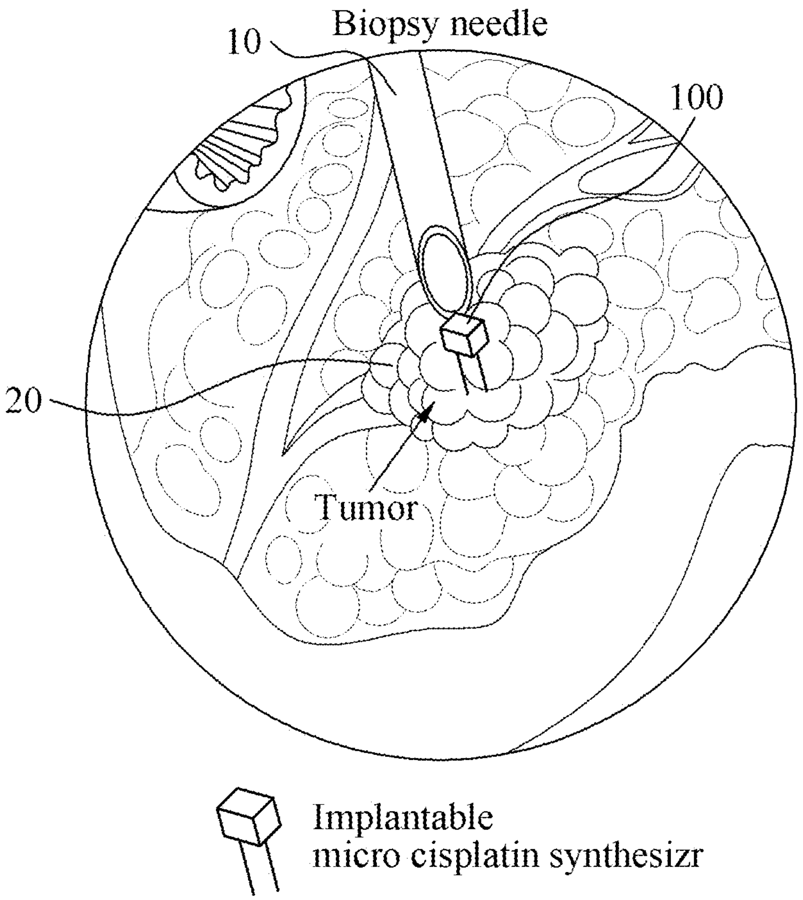
FIGS. 5A and 5B illustrate an example of driving an anticancer substance generator.
Figure 5B:
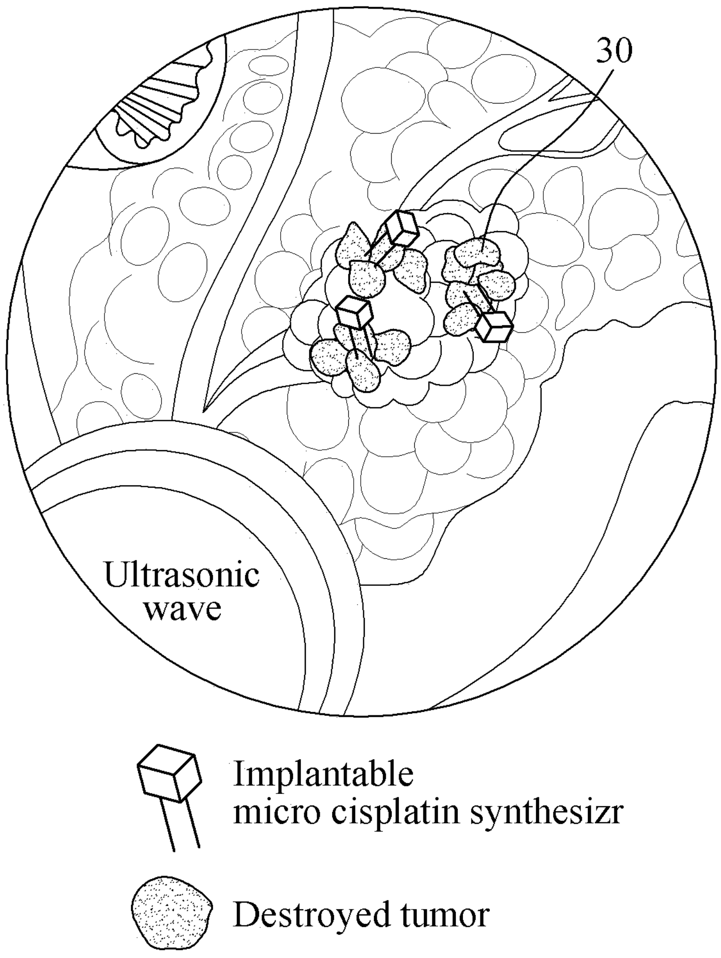

FIGS. 5A and 5B illustrate an example of driving the anticancer substance generator 100.

Referring to FIGS. 5A and 5B, the anticancer substance generator 100 may be injected into the living body through a biopsy needle 10. The anticancer substance generator 100 may have an adjustable size to be delivered into the living body through the biopsy needle 10. For example, although a size of the anticancer substance generator 100 may be similar to a size of a grain of rice, it is provided as an example only and the example embodiment is not limited thereto.

The anticancer substance generator 100 may be injected into the living body and may receive the signal generated by the signal generator 200. The anticancer substance generator 100 may convert the received signal to electric energy. The anticancer substance generator 100 may cause an electrolysis reaction in the body fluid of the living body present around the anticancer substance generator 100 using the electric energy.

In the electrolysis process, an oxidation reaction of metal may occur in the anode electrode of the anticancer substance generator 100. For example, when the anode electrode contains platinum, an oxidation reaction represented as in Formula 1 may occur.

$$Pt \rightarrow Pt^{4+} + 4e^- \quad \text{[Formula 1]}$$

Also, ionized materials contained in the body fluid of the living body present around the anode electrode may lose electrons by the anode electrode. In this process, oxygen gas and chlorine gas may be generated. A generation process of oxygen gas and chlorine gas may be represented as Formula 2 and Formula 3.

$$2OH^- \rightarrow H_2O + \frac{1}{2}O_2(g) + 2e^- \quad \text{[Formula 2]}$$

$$2Cl^- \rightarrow Cl_2 + 2e^- \quad \text{[Formula 3]}$$

Platinum cations may react with chlorine anions present in the body fluid of the living body. Through the reaction, a precursor of cisplatin, $[PtCl_4]^{2-}$, $[Pt(NH_3)Cl_3]^-$, $[Pt(NH_3)_3Cl]^+$, may be generated.

Figure 6:
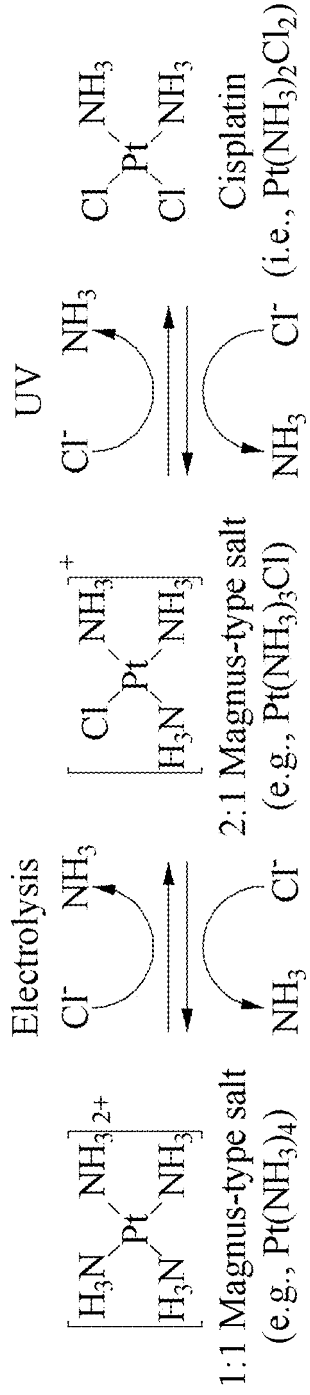
FIG. 6 illustrates a synthesis process of cisplatin.

FIG. 6 illustrates a synthesis process of cisplatin.

Referring to FIG. 6, the light emitter 140 may emit light to a precursor and the body fluid of the living body. Emission of ultraviolet light may promote a chemical reaction between the precursor and ionized materials present in the body fluid of the living body. Due to a chemical reaction between the precursor and ammonia ions $$(NH_3^+)$$

present in the body fluid of the living body, cisplatin $((cis)PtCl_2(NH_3)_2)$ may be synthesized. The aforementioned chemical reaction may be represented as FIG. 6.

In the aforementioned example, cisplatin is used as an example. However, the example embodiment is not limited thereto. When the electrode pair 130 contains a platinum material, the anticancer substance generator 100 may generate another platinum-based anticancer substance using platinum cations.

As the anticancer substance generator 100 generates the anticancer substance, a portion of cancer cells may be destroyed and become dead cells 30.

Figure 7:
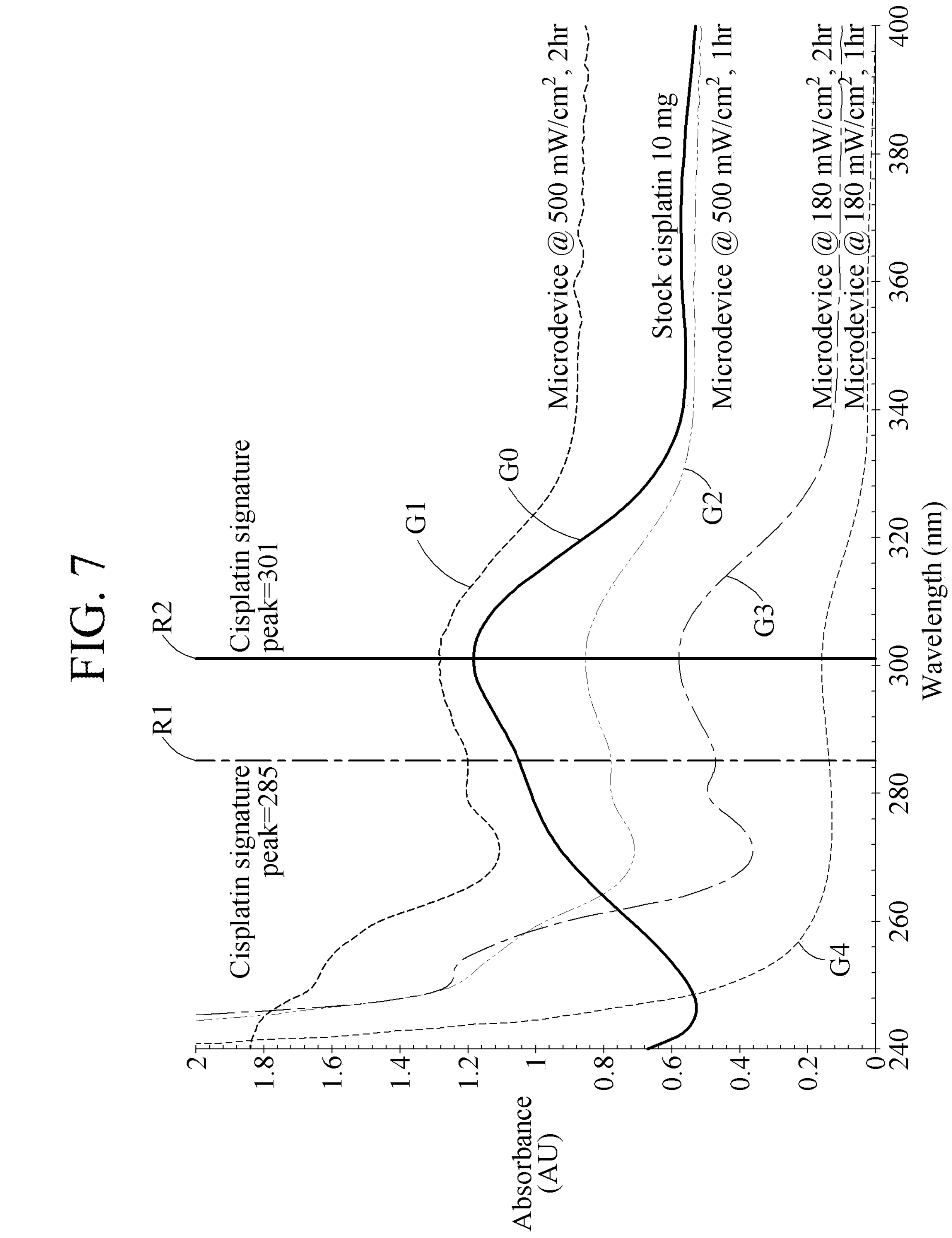
FIG. 7 is a graph showing experimental results of capability of generating an anticancer substance by an anticancer substance generation device.

FIG. 7 is a graph showing experimental results of capability of generating an anticancer substance by an anticancer substance generation device.

The graph represents an absorption spectrum. R1 represents a first region in which a peak value is formed in the absorption spectrum of cisplatin and may be near a wavelength band of about 285 nm. R2 represents a second region in which a peak value is formed in the absorption spectrum of cisplatin and may be near a wavelength band of about 301 nm.

Graph G0 represents the absorption spectrum of 10 mg of stock cisplatin. It can be verified from the graph G0 that an absorbance is partially high in regions R1 and R2, and particularly, it can be verified that the absorbance is maximum in the region R2.

Graph G1 represents the absorption spectrum near the anticancer substance generator 100 when the signal generator 200 generated an ultrasonic signal of 500 mW/cm$^2$ for two hours. Graph G2 represents the absorption spectrum near the anticancer substance generator 100 when the signal generator 200 generated an ultrasonic signal of 500 mW/cm$^2$ for 1 hour. Graph G3 represents the absorption spectrum near the anticancer substance generator 100 when the signal generator 200 generated an ultrasonic signal of 180 mW/cm$^2$ for 2 hours. The graph G1 represents the absorption spectrum near the anticancer substance generator 100 when the signal generator 200 generated an ultrasonic signal of 180 mW/cm$^2$ for 1 hour.

Referring to FIG. 7, as the signal generator 200 increases intensity of the ultrasonic signal and also increases an amount of time for generating the ultrasonic signal, it can be verified that more cisplatin is synthesized. Referring to the graph G2, when the signal generator 200 generated the ultrasonic signal of 500 mW/cm$^2$ for 1 hour, it can be verified that the absorption spectrum of the anticancer substance generator 100 is almost similar to the absorption spectrum of 10 mg of stock cisplatin. Referring to the graph G1, when the signal generator 200 generated the ultrasonic signal of 500 mW/cm$^2$ for 2 hours, it can be verified that a shape of the absorption spectrum near the anticancer substance generator 100 is almost similar to a shape of the absorption spectrum of 10 mg of stock cisplatin and that a scale of the absorption spectrum near the anticancer substance generator 100 is greater than a scale of the absorption spectrum of 10 mg of stock cisplatin. That is, when the signal generator 200 generates the ultrasonic signal of 500 mW/cm$^2$ for 2 hours, more effect may be expected than local administration of 10 mg of existing stock cisplatin.

Figure 8:
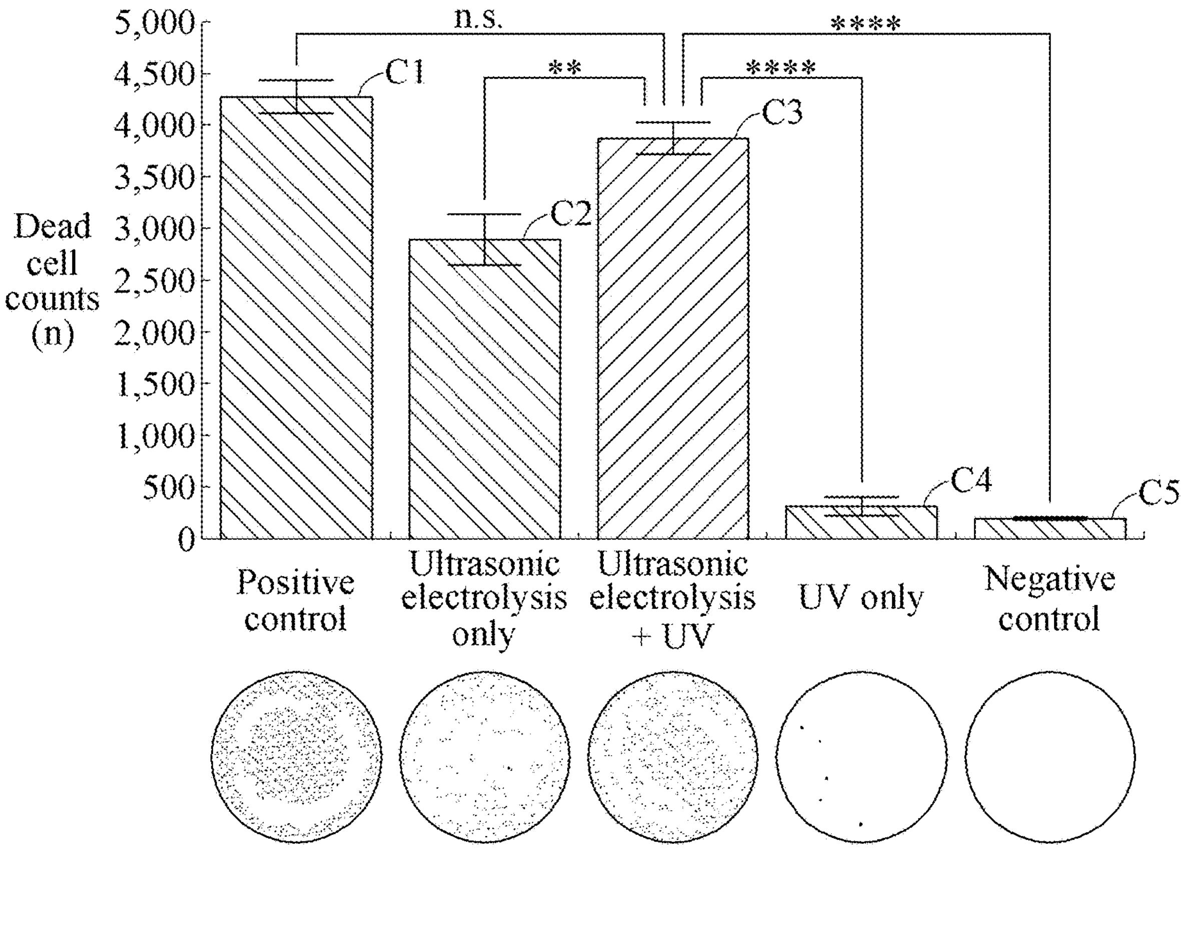
FIG. 8 is a graph showing comparative test results for anticancer performance against in-vitro cultured cancer cells.

FIG. 8 is a graph showing comparative test results for anticancer performance against in-vitro cultured cancer cells.

Graph C1 of FIG. 8 shows dead cell counts of cancer cells when the anticancer substance generator 100 performed electrolysis and, here, emitted ultraviolet (UV) light using a separate light source. Graph C2 shows dead cell counts of cancer cells when the anticancer substance generator 100 performed only the electrolysis. Graph C3 shows dead cell counts of cancer cells when the anticancer substance generator 100 autonomously performed the electrolysis and emitted the ultraviolet light by installing the light emitter 140 and the platinum electrode pair 130 in the anticancer substance generator 100. Graph C4 represents dead cell counts of cancer cells when the anticancer substance generator 100 emitted the ultraviolet light only without performing the electrolysis. Graph C5 represents dead cell counts of cancer cells when the anticancer substance generator 100 was not operated.

Referring to FIG. 8, it can be verified that when the anticancer substance generator 100 emitted only the ultraviolet light C4, more cancer cells died compared to when no operation was made, but the effect was insignificant. Also, it can be verified that when the anticancer substance generator 100 performed only the electrolysis C2, an excellent anticancer effect was exhibited compared to the case of emitting only the ultraviolet light (C4). It can be verified that when the anticancer substance generator 100 performed the electrolysis and emitted ultraviolet light C3, the most excellent anticancer effect was acquired compared to other cases C2, C4 and C5. In particular, even compared to an ideal case C1 (a situation in which it is significantly difficult to generate in vivo) using the anticancer substance generator 100 and the separate light source, it can be verified that the anticancer performance of the case C2 using the anticancer substance generator 100 is not far behind.

Figure 9:
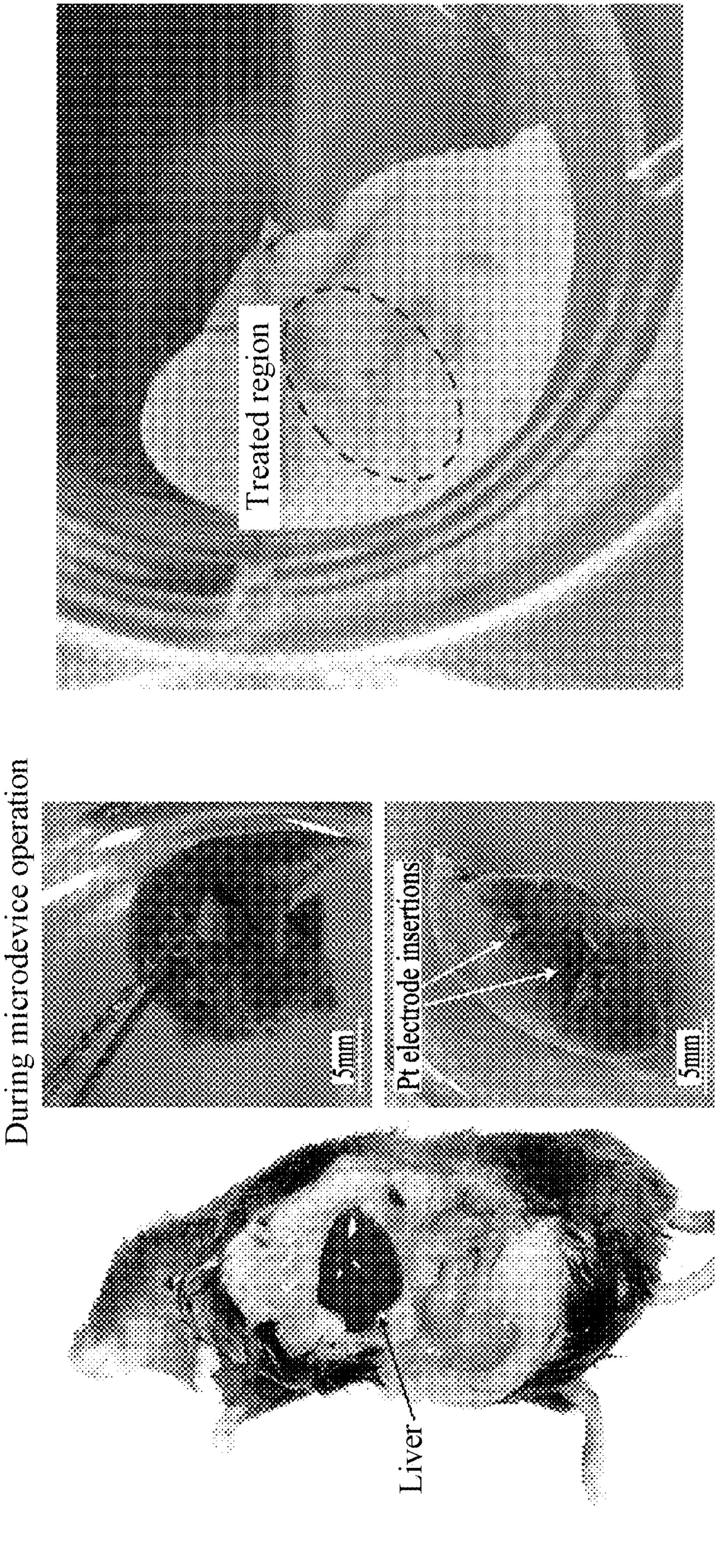
FIG. 9 illustrates the effect of an anticancer substance generation device on the liver tissue ex vivo from an experimental mouse.

FIG. 9 illustrates the effect of an anticancer substance generation device on the liver tissue ex vivo from an experimental mouse.

Referring to FIG. 9, the experimental results for the liver tissue ex vivo from the mouse show that the anticancer substance generator 100 of the anticancer substance generation device generates an anticancer substance through electrolysis and additional chemical reaction and kills cancer cells.

The anticancer substance generation device and method according to example embodiments are described with reference to FIGS. 1 to 9. According to at least one example embodiment, it is possible to deliver energy to an anticancer substance generator injected into a living body with high efficiency using an ultrasonic wave. According to at least one example embodiment, a non-toxic anticancer substance generator with a sufficiently small size may be injected into a living body and locally generate an anticancer substance, thereby minimizing side effects or damage to the living body. According to at least one example embodiment, an anticancer substance generator may effectively generate a sufficient amount of anticancer substance by causing electrolysis and by promoting a chemical reaction through emission of ultraviolet light.

According to at least one example embodiment, it is possible to deliver energy to an anticancer substance generator injected into a living body with high efficiency using an ultrasonic wave. According to at least one example embodiment, a non-toxic anticancer substance generator with a sufficiently small size may be injected into a living body and locally generate an anticancer substance, thereby minimizing side effects or damage to the living body. According to at least one example embodiment, an anticancer substance generator may effectively generate a sufficient amount of anticancer substance by causing electrolysis and by promoting a chemical reaction through emission of ultraviolet light.

Although the example embodiments are described with reference to the drawings, it will be understood by one of ordinary skill in the art that various technical modifications and alterations may be made based on the aforementioned description. For examples, although the methods may be implemented in different sequence and/or components of systems, structures, apparatuses, circuits, etc., may be combined or integrated in different form or may be replaced with other components or equivalents, appropriate results may be achieved.

What is claimed is:

1. A device for inserting into a living body and generating an anticancer substance, the device comprising:

an electric energy converter configured to receive an external signal and to convert the external signal to electric energy;

at least one electrode pair configured to cause electrolysis in a body fluid inside the living body using the electric energy converted by the electric energy converter, wherein the at least one electrode pair contains platinum, and at least a portion of the at least one electrode pair generates platinum cations in the electrolysis process; and a light emitter configured to emit light to a precursor of cisplatin generated based on the platinum cations using the electric energy converted by the electric energy converter, wherein the light emitter is configured to emit ultraviolet light to the precursor of cisplatin to produce cisplatin.

2. The device of claim 1, wherein the electric energy converter is configured to receive an ultrasonic signal generated outside the living body and to convert the ultrasonic signal to the electric energy.

3. The device of claim 2, wherein the electric energy converter includes a piezoelectric element configured to receive the ultrasonic signal.

4. The device of claim 1, wherein cisplatin is a platinum-based anticancer substance.

5. The device of claim 1, further comprising:

a rectifying circuit configured to convert current generated by the electric energy converter to one-way current and to supply the one-way current to the at least one electrode pair.

6. The device of claim 5, wherein the light emitter is directly connected to the electric energy converter.

7. The device of claim 6, wherein the light emitter is connected to the electric energy converter through the rectifying circuit.

8. The device of claim 7, wherein the electric energy converter and the rectifying circuit are installed on a substrate.

9. The device of claim 7, further comprising a cover installed on the substrate to protect the light emitter and the rectifying circuit.

10. The device of claim 1, wherein the light emitter is configured to induce a chemical reaction between the precursor of cisplatin generated based on the platinum cations and ions contained in the body fluid of the living body by emitting the ultraviolet light to the precursor of cisplatin.

11. The device of claim 1, wherein the device is configured and/or sized to be injected into the living body through a biopsy needle.

12. The device of claim 11, wherein the device has a size similar to a size of a grain of rice.

13. The device of claim 1, wherein the device is implantable in the living body or in the liver tissue of the living body.

14. A device for generating an anticancer substance in a living body, the device comprising:

a signal generator configured to generate an energy transfer signal outside the living body;

an anticancer substance generator configured to insert into the living body and to generate an anticancer substance using the energy transfer signal received from the signal generator, wherein the anticancer substance generator comprises an electric energy converter configured to receive an external signal and to convert the external signal to electric energy;

at least one electrode pair configured to cause electrolysis in a body fluid inside the living body using the electric energy converted by the electric energy converter, wherein the at least one electrode pair contains platinum, and at least a portion of the at least one electrode pair generates platinum cations in the electrolysis process; and a light emitter configured to emit light to a precursor of cisplatin generated based on the platinum cations using the electric energy converted by the electric energy converter, wherein the light emission module is configured to emit ultraviolet light to the precursor of cisplatin to produce cisplatin.

15. The device of claim 14, wherein the signal generator is configured to generate an ultrasonic signal, and the electric energy converter is configured to receive the ultrasonic signal generated outside the living body and to convert the ultrasonic signal to the electric energy.

16. The device of claim 15, wherein the electric energy converter includes a piezoelectric element configured to receive the ultrasonic signal.

17. The device of claim 14, wherein cisplatin is a platinum-based anticancer substance.

18. The device of claim 14, wherein the anticancer substance generator further comprises:

a rectifying circuit configured to convert current generated by the electric energy converter to one-way current and to supply the one-way current to the at least one electrode pair.

19. The device of claim 14, wherein the light emitter is configured to induce a chemical reaction between the precursor of cisplatin generated based on the platinum cations and ions contained in the body fluid of the living body by emitting the ultraviolet light to the precursor of cisplatin.

* * * * *